(12) United States Patent
Warashina et al.

(10) Patent No.: US 10,016,508 B2
(45) Date of Patent: Jul. 10, 2018

(54) COMPOSITION FOR HOT-MELT EXTRUSION AND METHOD FOR PRODUCING HOT-MELT EXTRUSION PRODUCT USING SAME

(71) Applicant: Shin-Etsu Chemical Co., Ltd., Tokyo (JP)

(72) Inventors: Shogo Warashina, Niigata-ken (JP); Fumie Kusaki, Tokyo (JP); Kazuki Kikuchi, Niigata-ken (JP); Sakae Obara, Tokyo (JP); Naosuke Maruyama, Niigata-ken (JP)

(73) Assignee: Shin-Etsu Chemical Co., Ltd., Tokyo (JP)

(*) Notice: Subject to any disclaimer, the term of this patent is extended or adjusted under 35 U.S.C. 154(b) by 0 days.

(21) Appl. No.: 14/294,258

(22) Filed: Jun. 3, 2014

(65) Prior Publication Data

US 2014/0357681 A1    Dec. 4, 2014

(30) Foreign Application Priority Data

Jun. 3, 2013 (JP) ............... 2013-116836
Nov. 28, 2013 (JP) ............... 2013-246178

(51) Int. Cl.

| | | |
|---|---|---|
| A61K 31/4422 | (2006.01) |
| A61K 47/38 | (2006.01) |
| C08B 11/193 | (2006.01) |
| C08B 11/20 | (2006.01) |
| C08B 13/00 | (2006.01) |
| C08L 1/32 | (2006.01) |
| A61K 9/14 | (2006.01) |
| C08J 3/20 | (2006.01) |
| A61K 31/496 | (2006.01) |

(52) U.S. Cl.
CPC ............. *A61K 47/38* (2013.01); *A61K 9/146* (2013.01); *A61K 31/4422* (2013.01); *A61K 31/496* (2013.01); *C08B 11/193* (2013.01); *C08B 11/20* (2013.01); *C08B 13/00* (2013.01); *C08J 3/201* (2013.01); *C08L 1/32* (2013.01); *C08J 2301/32* (2013.01)

(58) Field of Classification Search
None
See application file for complete search history.

(56) References Cited

U.S. PATENT DOCUMENTS

| | | | |
|---|---|---|---|
| 3,852,421 A | 12/1974 | Cunningham | |
| 4,226,981 A | 10/1980 | Onda et al. | |
| 4,266,981 A | 5/1981 | Tsao et al. | |
| 8,207,232 B2 * | 6/2012 | Babcock et al. | 514/781 |
| 2003/0186952 A1 | 10/2003 | Crew et al. | |
| 2008/0262107 A1 * | 10/2008 | Babcock et al. | 514/781 |
| 2011/0034478 A1 | 2/2011 | Fang et al. | |
| 2011/0123627 A1 * | 5/2011 | Fang et al. | 424/489 |
| 2012/0252819 A1 * | 10/2012 | Padval et al. | 514/255.03 |
| 2013/0102691 A1 | 4/2013 | Miller et al. | |

FOREIGN PATENT DOCUMENTS

| | | |
|---|---|---|
| JP | 54-061282 | 5/1979 |
| JP | 2004-262999 A | 9/2004 |
| JP | 2005-523895 A | 8/2005 |
| JP | 2008-501009 A | 1/2008 |
| JP | 2011-516612 A | 5/2011 |
| WO | WO 03/063832 A1 | 8/2003 |
| WO | WO 03/077827 A1 | 9/2003 |
| WO | WO 2005/115330 A2 | 12/2005 |
| WO | WO 2007/029660 A1 | 3/2007 |
| WO | WO 2008051794 * | 5/2008 |
| WO | WO 2009/129300 A2 | 10/2009 |
| WO | WO 2011/159626 A | 12/2011 |
| WO | WO-2012/122279 A1 | 9/2012 |

OTHER PUBLICATIONS

Obara et al. "Application Studies of L-HPC and HPMCAS for Pharmaceutical Dosage Forms" (google date of Apr. 2012).*

(Continued)

*Primary Examiner* — Robert A Wax
*Assistant Examiner* — Danah Al-Awadi
(74) *Attorney, Agent, or Firm* — Alston & Bird LLP

(57) ABSTRACT

Provided are a composition for hot-melt extrusion which can be hot-melt extruded at a temperature lower than a conventional temperature and therefore free of heat-induced deactivation of a drug; and a method for producing a hot-melt extrusion product which is simpler than a spray-drying method. More specifically, provided is a composition for hot-melt extrusion including a drug and hypromellose acetate succinate (HPMCAS) having a hydroxypropoxy molar substitution of 0.40 or more. Also provided is a method for producing a hot-melt extrusion product including a step of hot-melt extruding a composition for hot-melt extrusion including a drug and hypromellose acetate succinate having a hydroxypropoxy molar substitution of 0.40 or more at a hot-melt temperature of melting temperature of the hypromellose acetate succinate or higher, or at a hot-melt temperature equal to or higher than a temperature at which both the hypromellose acetate succinate and the drug become melted.

19 Claims, No Drawings

(56) References Cited

OTHER PUBLICATIONS

*Hypromellose Acetate Succinate*, Supp I, JP XVI, Official Monographs, Japanese Pharmacopeia 16$^{th}$ Edition (Sep. 27, 2012), pp. 2426-2428.
International Search Report and Written Opinion from International Application No. PCT/JP2014/064711 dated Sep. 9, 2014.
Office Action from European Patent Application No. 14170863.6 dated Jun. 1, 2016.
Liang-liang, Z. et al., *Determination of Acyl Content in Hydroxypropyl Methylcellulose Acetate Succinate by High Performance Liquid Chromatography* (Apr. 30, 2012), 71-75.
Office Action for Chinese Application No. 201410242677.6 dated Mar. 9, 2016.
Extended European Search Report from corresponding European Patent Application No. 14806945.3 dated Jan. 25, 2017, 6 pages.
Crowley, Michael M. et al. "Pharmaceutical Applications of Hot-Melt Extrusion: Part 1." Drug Development and Industrial Pharmacy, 33:909-926, 2007, 19 pages.
Rowe, Raymond C. et al. "Handbook of Pharmaceutical Excipients: Sixth Edition." Pharmaceutical Press, London, UK and American Pharmacists Association, Washington, DC; 2009; pp. 330-332.
Tanno, F. et al. "Evaluation of Hypromellose Acetate Succinate (HMPCAS) as a Carrier in Solid Dispersions." Drug Development and Industrial Pharmacy®, vol. 30, No. 1, 2004, pp. 9-17.
Floyd, F.L. Ho et al.; "Determination of Molar Substitution and Degree of Substitution of Hydroxypropyl Cellulose By Nuclear Magnetic Resonance Spectrometry"; *Analytical Chemistry*; vol. 44, No. 1; Jan. 1, 1972; p. 178-181; XP5513137.
Extended European Search Report from European Patent Application No. 14170863.6, dated Sep. 17, 2014.

\* cited by examiner

COMPOSITION FOR HOT-MELT EXTRUSION AND METHOD FOR PRODUCING HOT-MELT EXTRUSION PRODUCT USING SAME

FIELD

The present invention relates to a composition for hot-melt extrusion and a method for producing a hot-melt extrusion product using the composition.

BACKGROUND

A method for producing a preparation through melt extrusion of a mixture of a drug and a polymer under heating has recently attracted attentions.

For example, a solid dispersion obtained by solidifying a poorly water-soluble drug and a polymer through hot-melt extrusion improves bioavailability of the drug because the drug is molecularly dispersed in an amorphous form in the polymer carrier and the apparent solubility of the drug shows a marked increase. Further, the hot-melt extrusion can avoid using a solvent so that it has various advantages. For example, the hot-melt extrusion can be applied to a drug not stable in water, is safe and environmentally friendly because of unnecessity of solvent recovery, can save energy spent for the solvent recovery, and provides a working environment with improved safety. Still further, differing from conventional batch production, this method permits continuous production so that it has attracted attentions also from the standpoint of hourly productivity and consumption energy.

One example of the polymers to be used for hot-melt extrusion is hypromellose acetate succinate (which may hereinafter be called "HPMCAS") which is obtained by introducing four substituents in total in a cellulose skeleton, more specifically, introducing two substituents, that is, a methoxy group (—$OCH_3$) and a hydroxypropoxy group (—$OC_3H_6OH$) to form an ether structure and two substituents, that is, an acetyl group (—$COCH_3$) and a succinyl group (—$COC_2H_4COOH$) to form an ester structure.

The content of each of the substituents of HPMCAS listed in the Japanese Pharmacopoeia 16th Edition is specified as follows (the Japanese Pharmacopoeia 16th Edition, Supplement I, Official Monographs, "Hypromellose Acetate Succinate").

TABLE 1

|  | Content (weight %) | Molar substitution (MS)*1 |
|---|---|---|
| Methoxy group | 12.0 to 28.0 | 0.73 to 2.83 |
| Hydroxypropoxy group | 4.0 to 23.0 | 0.10 to 1.90 |
| Acetyl group | 2.0 to 16.0 | 0.09 to 2.30 |
| Succinyl group | 4.0 to 28.0 | 0.08 to 1.78 |

*1: The term "molar substitution" means an average number of moles of respective group added per glucose ring unit of cellulose.

As a solid dispersion comprising HPMCAS, there is a report on, for example, a solid dispersion composition obtained through hot-melt extrusion of a preliminary mixture obtained by adding water to HPMCAS (commercially available AS-LF having a molar substitution of from 0.16 to 0.35), where an addition of water decreases the glass transition temperature or softening temperature of the HPMCAS or poorly water-soluble drug (WO 2003/077827).

Further, there are proposed a method for producing a preparation through hot-melt extrusion of posaconazole which is a poorly water-soluble drug and HPMCAS (commercially available AS-MF and AS-MG, each having a molar substitution of from 0.15 to 0.34) (Japanese Phase Publication No. 2011-516612T of WO 2009/129300); and a method for producing a preparation through hot-melt extrusion of CETP (cholesteryl ester transfer protein) inhibitor, which is a poorly water-soluble lipid inhibitor, and HPMCAS (commercially available AS-MF having a molar substitution of from 0.15 to 0.34) (Japanese Phase Publication No. 2005-523895T of WO 2003/063832).

Further, there is proposed a method for spray-drying a solid dispersion composition comprising a poorly water-soluble drug and HPMCAS having a hydroxypropoxy molar substitution of 0.25, a succinyl molar substitution of 0.02 or more, an acetyl molar substitution of 0.65 or more, a total molar substitution of the acetyl and succinyl groups of 0.85 or more, and a glass transition temperature of from 131 to 146° C. at 0% RH (Japanese Phase Publication No. 2008-501009T of WO 2005/115330). There is also proposed a method for spray-drying a solid dispersion composition comprising a poorly water-soluble drug and HPMCAS having a hydroxypropoxy molar substitution of not more than 0.21, a methoxy molar substitution of not more than 1.45, and a total molar substitution of the acetyl and succinyl groups of not less than 1.25 (WO2011/159626).

SUMMARY

In recent years, there has been a demand for a more convenient method for preparing a solid dispersion, so that a lower hot-melt temperature during hot-melt extrusion has become necessary.

The method described in WO2003/077827, however, causes problems in some cases because water is a poor solvent for a poorly water-soluble drug. For example, water may enhance the crystallinity of the drug, thereby preventing the drug from becoming amorphous; the poorly water-soluble drug is deactivated by heat or humidity during high-temperature treatment; or the drug or carrier is apt to be hydrolyzed under a humid condition owing to the influence of heat and water and is deactivated.

On the other hand, in the methods described in Japanese Phase Publication No. 2011-516612T of WO 2009/129300 and Japanese Phase Publication No. 2005-523895T of WO 2003/063832, the hot-melt temperature is higher than the glass transition temperature (Tg) of HPMCAS so that there is concern that the poorly water-soluble drug and HPMCAS are thermally decomposed and deactivated.

In the methods described in WO 2011/159626 and Japanese Phase Publication No. 2008-501009T of WO 2005/115330, high-temperature hot-melt extrusion causes problems such as deactivation of the poorly water-soluble drug caused by a free acid generated by thermal decomposition of HPMCAS, or thermal decomposition of the poorly water-soluble drug. In a spray-drying method or spray-coating method conventionally known as a method for producing a solid dispersion, a decrease of the glass transition temperature of a polymer used as a carrier may cause attachment of HPMCAS to a wall surface of a spray apparatus or fusion bonding of powders of the solid dispersion thus obtained so that an approach to decrease the glass transition temperature has not been investigated.

In view of such circumstances, the invention has been made. According to the invention, provided are a composition for hot-melt extrusion which can be hot-melt extruded at a temperature lower than a conventional temperature and which is therefore free of drug deactivation due to heat or the like and has high supersaturation maintaining capacity; and a method for producing a hot-melt extrusion product which can produce a hot-melt extrusion product more conveniently than a spray-drying method.

The present inventors have carried out an extensive investigation in order to overcome the above-mentioned problems. As a result, it has been found that by adjusting the molar substitution of the hydroxypropoxy group, among four substituents of HPMCAS, to fall within a predetermined range, the resulting HPMCAS has a lower glass transition temperature (Tg) than that of a conventional HPMCAS and a hot-melt extrusion product can be obtained at a lower hot-melt extrusion temperature; and that by adjusting the molar ratio of acetyl groups to succinyl groups to fall within a predetermined range, the resulting product has higher supersaturation maintaining capacity, leading to the completion of the invention.

According to the present invention, provided is a composition for hot-melt extrusion comprising a drug and hypromellose acetate succinate (HPMCAS) having a hydroxypropoxy molar substitution of 0.40 or more and preferably having a molar ratio of acetyl groups to succinyl groups of from 1.6 to 4.0. According to the present invention, also provided is a method for producing a hot-melt extrusion product comprising a step of hot-melt extruding a composition for hot-melt extrusion comprising a drug and hypromellose acetate succinate having a hydroxypropoxy molar substitution of 0.40 or more and preferably having a molar ratio of acetyl groups to succinyl groups of from 1.6 to 4.0 at a hot-melt temperature of melting temperature of the hypromellose acetate succinate or higher, or at a hot-melt temperature equal to or higher than a temperature at which both the hypromellose acetate succinate and the drug become melted.

According to the invention, hot-melt extrusion can be carried out at a temperature lower than that for a conventional method so that free from deactivation of the drug due to heat or the like, a hot-melt extrusion product can be obtained by the method which is more convenient than spray-drying or the like. In addition, the hot-melt extrusion product can have higher supersaturation maintaining capacity higher than that of a product obtained by a conventional method.

DETAILED DESCRIPTION

The invention will hereinafter be described more specifically.

The hydroxypropoxy molar substitution of the HPMCAS is 0.40 or more, preferably from 0.40 to 1.50, more preferably from 0.40 to 1.0, still more preferably from 0.40 to 0.90. When the hydroxypropoxy molar substitution is less than 0.40, the hot-melt extrusion temperature becomes high and hydrolysis occurs due to thermal decomposition of the hypromellose acetate succinate. Some of the ester groups are then released from the cellulose skeleton to generate acetic acid and succinic acid, which deactivate the drug through the interaction with the drug.

The content of the substituents of the HPMCAS including a hydroxypropoxy group can be determined by the method described in the Japanese Pharmacopoeia 16th Edition, Supplement I, Official Monographs, "Hypromellose Acetate Succinate".

The glass transition temperature (Tg) of the HPMCAS is preferably 115° C. or lower, more preferably from 60 to 115° C., still more preferably from 70 to 100° C. When the glass transition point is higher than 115° C., the hot-melt extrusion temperature also becomes high and there is a possibility that the above-mentioned thermal decomposition occurs.

The glass transition temperature (Tg) is typically measured in the following manner by using a differential scanning calorimeter (DSC). Described specifically, an inflection point observed when 10 mg of HPMCAS is heated to 150° C. from room temperature at a heating rate of 10° C./min, once cooled to 25° C. at a cooling rate of 10° C./min, and then, heated again to 230° C. at a heating rate of 10° C./min, is designated as a glass transition temperature. Since the water content in a sample has an influence on the measured value of Tg, the glass transition temperature is thus measured in the absolute dry state.

The molar substitution of a methoxy group, which is a substituent of the HPMCAS other than the hydroxypropoxy group, is not particularly limited. It is preferably from 0.70 to 2.90, more preferably from 1.00 to 2.40, still more preferably from 1.4 to 1.9.

The acetyl molar substitution of the HPMCAS is also not particularly limited. It is preferably from 0.10 to 2.50, more preferably from 0.10 to 1.00, still more preferably from 0.40 to 0.95.

The succinyl molar substitution of the HPMCAS is also not particularly limited. It is preferably from 0.10 to 2.50, more preferably from 0.10 to 1.00, still more preferably from 0.10 to 0.60.

A molar ratio of acetyl groups to succinyl groups is preferably from 1.6 to 4.0, more preferably from 1.8 to 3.8, from the standpoint of maintaining the supersaturation state of the drug as long as possible.

A viscosity at 20° C. of the 2% by weight HPMCAS in a dilute aqueous sodium hydroxide solution having a sodium hydroxide concentration of 0.1 mol/L is preferably from 1.1 to 20 mPa·s, more preferably from 1.5 to 3.6 mPa·s. When the viscosity is less than 1.1 mPa·s, a sufficient shear force may not be applied due to a too low melt viscosity during hot-melt extrusion, which may lead to idling of a piston or screw, or difficulty in extrusion from an outlet port. When the viscosity is more than 20 mPa·s, the viscosity of the composition for hot-melt extrusion may become too high so that a torque applied to a piston or screw may become too large, which may lead to unrotation of the piston or screw or safety stop of the machine. The viscosity can be measured using the method described in the Japanese Pharmacopoeia 16th Edition, General Test of HPMCAS.

HPMCAS can be prepared using, for example, the method described in JP 54-061282A. Described specifically, hypyromellose (another name: hydroxypropylmethyl cellulose, which may hereinafter be called "HPMC") used as a raw material is dissolved in glacial acetic acid. Acetic anhydride and succinic anhydride as esterification agents and sodium acetate as a reaction catalyst are added thereto, and the resulting mixture is reacted under heating. After completion of the reaction, a large amount of water is added to the reaction mixture to precipitate HPMCAS. The resulting precipitate is washed with water and then dried. When HPMC having a hydroxypropoxy molar substitution of 0.40 or more is used, the HPMCAS thus prepared has a hydroxypropoxy molar substitution of 0.40 or more.

The drug is not particularly limited insofar as it is orally administrable. Examples of such a drug include central nervous system drugs, circulatory system drugs, respiratory system drugs, digestive system drugs, antibiotics, antitussive and expectorant drugs, antihistamine drugs, antipyretic, analgesic and anti-inflammatory drugs, diuretic drugs, autonomic drugs, antimalarial drugs, anti-diarrheal drugs, psychotropic drugs, and vitamins and derivatives thereof.

Examples of the central nervous system drugs include diazepam, idebenone, aspirin, ibuprofen, paracetamol, naproxen, piroxicam, diclofenac, indomethacin, sunlindac, lorazepam, nitrazepam, phenytoin, acetaminophen, ethenzamide, ketoprofen and chlordiazepoxide.

Examples of the circulatory system drugs include molsidomine, vinpocetine, propranolol, methyldopa, dipyridamole, furosemide, triamterene, nifedipine, atenolol, spironolactone, metoprolol, pindolol, captopril, isosorbide nitrate, delapril hydrochloride, meclofenoxate hydrochloride, diltiazem hydrochloride, etilefrine hydrochloride, digitoxin, propranolol hydrochloride and alprenolol hydrochloride.

Examples of the respiratory system drugs include amlexanox, dextromethorphan, theophylline, pseudoephedrine, salbutamol and guaifenesin.

Examples of the digestive system drugs include benzimidazole-based drugs having an anti-ulcer action such as 2-[[3-methyl-4-(2,2,2-trifluoroethoxy)-2-pyridyl]methylsulfinyl]benzimidazole and 5-methoxy-2-[(4-methoxy-3,5-dimethyl-2-pyridyl)methylsulfinyl]benzimidazole; cimetidine; ranitidine; pirenzepine hydrochloride; pancreatin; bisacodyl; and 5-aminosalicyclic acid.

Examples of the antibiotics include talampicillin hydrochloride, bacampicillin hydrochloride, cefaclor and erythromycin.

Examples of the antitussive and expectorant drugs include noscapine hydrochloride, carbetapentane citrate, dextromethorphan hydrobromide, isoaminile citrate and dimemorfan phosphate.

Examples of the antihistamine drugs include chlorpheniramine maleate, diphenhydramine hydrochloride and promethazine hydrochloride.

Examples of the antipyretic, analgesic and anti-inflammatory drugs include ibuprofen, diclofenac sodium, flufenamic acid, sulpyrine, aspirin and ketoprofen.

Examples of the diuretic drugs include caffeine.

Examples of the autonomic drugs include dihydrocodeine phosphate, dl-methylephedrine hydrochloride, propranolol hydrochloride, atropine sulfate, acetylcholine chloride and neostigmine.

Examples of the antimalarial drugs include quinine hydrochloride.

Examples of the anti-diarrheal drugs include loperamide hydrochloride.

Examples of the psychotropic drugs include chlorpromazine.

Examples of the vitamins and derivatives thereof include Vitamin A, Vitamin B1, fursultiamine, Vitamin B2, Vitamin B6, Vitamin B12, Vitamin C, Vitamin D, Vitamin E, Vitamin K, calcium pantothenate and tranexamic acid.

In particular, a poorly water-soluble drug can have improved solubility by using the HPMCAS of the invention as a carrier of a solid dispersion of the poorly water-soluble drug. The term "poorly water-soluble drug" means a drug expressed as "slightly soluble", "very slightly soluble", or "practically insoluble or insoluble" in water in accordance with the Japanese Pharmacopoeia 16th Edition. These terms mean the degree of dissolution when 1 g or 1 mL of a solid pharmaceutical in a beaker is subjected to addition of water, and is vigorously shaken at 20±5° C. for 30 seconds each time at 5-minute intervals. The term "slightly soluble" means that the volume of water required for dissolving it within 30 minutes is from 100 mL to less than 1000 mL. The term "very slightly soluble" means that the volume of water required for dissolving it within 30 minutes is from 1000 mL to less than 10000 mL. The term "practically insoluble or insoluble" means that the volume of water required for dissolving it within 30 minutes is 10000 mL and more.

In the above pharmaceutical test, the term "a poorly water-soluble drug is soluble" means that the drug is soluble or miscible in a solvent and fibers cannot be observed or if any, a trace amount of fibers can be observed from the resulting solution.

Specific examples of the poorly water-soluble drug include azole-based compounds such as itraconazole, ketoconazole, fluconazole and mitoconazole; dihydropyridine-based compounds such as nifedipine, nitrendipine, amlodipine, nicardipine, nilvadipine, felodipine and efonidipine; propionic acid-based compounds such as ibuprofen, ketoprofen and naproxen; and indoleacetic acid-based compounds such as indomethacin and acemetacin. Additional examples include griseofulvin, phenytoin, carbamazepine and dipypridamole.

A weight ratio of HPMCAS to a drug is not particularly limited. A weight ratio of HPMCAS to a drug is preferably from 1:0.01 to 1:100, more preferably from 1:0.1 to 1:10, still more preferably from 1:0.2 to 1:5, from the standpoint of storage stability in an amorphous form.

Further, according to the invention, the composition for hot-melt extrusion may comprise an additive. The additive includes a plasticizer and a surfactant for improving the extrusion property during the hot-melt extrusion.

Examples of the plasticizer include higher alcohols such as acetone, methanol, ethanol, isopropanol, cetyl alcohol and stearyl alcohol; polyols such as mannitol, sorbitol and glycerin; beeswax; triethyl citrate; alkylene glycols such as polyethylene glycol and propylene glycol; triacetin; dibutyl sebacate; glycerin monostearate; and monoglycerin acetate.

Examples of the surfactant include anionic surfactants such as sodium lauryl sulfate; nonionic surfactants such as diglyceride, poloxamer, polyoxyethylene sorbitan fatty acid esters (Tween 20, 60 and 80), glycerin fatty acid esters and propylene glycol fatty acid esters; and natural surfactants such as lecithin and sodium taurocholate. The amount of the plasticizer based on the HPMCAS is preferably 30% by weight or less, and the amount of the surfactant based on the HPMCAS is preferably 10% by weight or less, from the standpoint of storage stability.

The hot-melt extrusion product can be used as an oral solid preparation such as tablets, granules, fine granules and capsules, or oral film formulations, optionally combined with one or more various additives typically and conventionally used in this field such as an excipient, a binder, a disintegrant, a lubricant and an anti-aggregation agent.

Examples of the excipient include sugars such as sucrose, lactose, mannitol and glucose; starches; and crystalline celluloses.

Examples of the binder include polyvinyl alcohol, polyacrylic acid, polyvinylpyrrolidone, hydroxyethyl cellulose, hydroxypropylmethyl cellulose, hydroxypropyl cellulose, macrogols, gum arabic, gelatin and starches.

Examples of the disintegrant include low-substituted hydroxypropyl cellulose, carmellose or salt thereof, croscarmellose sodium, carboxymethyl starch sodium, crospovidone, crystalline cellulose and crystalline cellulose.carmellose sodium.

Examples of the lubricant and the anti-aggregation agent include talc, magnesium stearate, calcium stearate, colloidal silica, stearic acid, waxes, hydrogenated oil, polyethylene glycols and sodium benzoate.

The oral solid preparation thus obtained may be film-coated with a water-soluble coating agent such as methyl cellulose or hypromellose; or coated with an enteric coating agent such as hypromellose acetate succinate, hypromellose phthalate, or a methacrylate acrylate copolymer.

A method for producing a hot-melt extrusion product will hereinafter be described.

First, a composition for hot-melt extrusion is produced by mixing a drug, HPMCAS having a hydroxypropoxy molar substitution of 0.40 or more, and an optional component. The composition for hot-melt extrusion thus produced is extruded into a desired shape such as a circular or square shape as well as a columnar or film shape through a hot-melt extruder to obtain an extrusion product.

The hot-melt extruder is not particularly limited insofar as it is an extruder having a structure capable of applying a shear force to HPMCAS, a drug and an optional component with a piston or screw while heating for melting and kneading, and then extruding through the die. It is preferably a twin-screw extruder from a viewpoint of a more uniform extrusion product. Specific examples include "Capilograph" (uniaxial piston extruder) produced by Toyo Seiki Seisakusho, "Nano-16" (twin-screw extruder) produced by Leistritz, and "MiniLab" (twin-screw extruder) and "PharmaLab" (twin-screw extruder) produced by THERMO FISHER SCIENTIFIC™.

The hot-melt temperature is not particularly limited. It is preferably in a temperature range which allows the composition for hot-melt extrusion to be melted and extruded smoothly, while avoiding thermal decomposition of the drug and the polymer as much as possible. In other words, the hot-melt temperature is preferably equal to or higher than the melting temperature of the HPMCAS when a solid dispersion is not produced; and the hot-melt temperature is preferably equal to or higher than a temperature at which both the HPMCAS and the drug become melted when a solid dispersion is produced. In the same manner, when addition of the drug lowers the melting point of the HPMCAS, the hot-melt temperature is preferably equal to or higher than a temperature at which both of the HPMCAS and the drug become melted. More specifically, the hot-melt temperature is preferably from 50 to 250° C., more preferably from 60 to 200° C., still more preferably from 90 to 190° C. When the hot-melt temperature is less than 50° C., incomplete melting may impede extrusion. When the hot-melt temperature is more than 250° C., there are possibilities of reduction in molecular weight due to decomposition of the HPMCAS or the drug, and deactivation due to hydrolysis of the substituent.

The extrusion conditions are not particularly limited insofar as they permit extrusion of a composition for hot-melt extrusion having preferably a viscosity, during hot-melt extrusion, of from 1 to 100000 Pa·s. When a uniaxial piston extruder is used, the extrusion rate is preferably from 1 to 1000 mm/min, more preferably from 10 to 500 mm/min. When a twin-screw extruder is used, the screw rotation number is preferably from 1 to 1000 rpm, more preferably from 10 to 500 rpm. When the extrusion rate is less than 1 mm/min or the screw rotation number is less than 1 rpm, the residence time in the extruder becomes long, which may cause thermal decomposition. When the extrusion rate is more than 1000 mm/min or the screw rotation number is more than 1000 rpm, the hot-melt procedure during kneading may become insufficient, which may result in non-uniform molten state of the drug and the polymer in the hot-melt extrusion product.

After the extrusion, the hot-melt extrusion product is cooled after the die outlet port by natural cooling at room temperature (from 1 to 30° C.) or by blowing of cold air. It is desired to rapidly cool the hot-melt extrusion product preferably to a temperature of not higher than 50° C., more preferably to a temperature of not higher than room temperature (not higher than 30° C.) to minimize the thermal decomposition of the drug and to prevent recrystallization when the drug is in an amorphous form.

The hot-melt extrusion product after cooling may be optionally pelletized into pellets of from 0.1 to 5 mm by using a cutter, or optionally ground to regulate the particle size until it becomes granular or powdery. As for grinding, an impact grinder such as a jet mill, a knife mill and a pin mill is preferred because its structure prevents an increase in the temperature of the product therein. When the temperature inside the cutter or grinder becomes high, the HPMCAS is thermally softened and the particles adhere to each other so that it is preferred to grind the extrusion product while blowing cold air.

EXAMPLES

The invention will hereinafter be described in detail by Examples and Comparative Examples. However, it should not be construed that the invention is limited to or by them.

Synthesis of HPMCAS-1

The 6 kg of hypromellose (HPMC) having a hydroxypropoxy molar substitution of 0.97 and a methoxy molar substitution of 1.67 was added to 12 kg of glacial acetic acid in a 50-L kneader, and dissolved. Further, 3.7 kg of acetic anhydride, 2.0 kg of succinic anhydride and 4.8 kg of sodium acetate were added thereto and the resulting mixture was reacted at 85° C. for 5 hours. After addition of 6.7 kg of purified water and stirring, the resulting mixture was subjected to further addition of purified water to precipitate HPMCAS in granular form, and filtered to collect a crude HPMCAS. The crude HPMCAS was washed with purified water, dried and then sieved through a 10-mesh (opening: 1700 μm) to obtain HPMCAS-1 having final water content of 1.2% by weight.

The content of each substituent of the HPMCAS-1 thus obtained was measured using the method described in the Japanese Pharmacopoeia 16th edition, Supplement I. As a result, the hydroxypropoxy group content was 24.1% by weight (molar substitution of 1.00), the methoxy group content was 16.7% by weight (molar substitution of 1.67), the acetyl group content was 5.6% by weight (molar substitution of 0.40), and the succinyl group content was 16.4% by weight (molar substitution of 0.50).

Synthesis of HPMCAS-2 to 11

Various HPMCAS-2 to 11 shown in Table 2 were obtained in the same manner as in Synthesis of HPMCAS-1 by using raw material HPMCs different in the contents of substituents and changing the amounts of acetic anhydride and succinic anhydride.

TABLE 2

| | Molar substitution | | | | Molar ratio |
|---|---|---|---|---|---|
| | Hydroxy-propoxy group | Methoxy group | Acetyl group | Succinyl group | Ratio of acetyl to succinyl |
| HPMCAS-1 | 1.00 | 1.67 | 0.40 | 0.50 | 0.80 |
| HPMCAS-2 | 0.84 | 1.58 | 0.64 | 0.43 | 1.49 |

TABLE 2-continued

|  | Molar substitution | | | | Molar ratio |
| --- | --- | --- | --- | --- | --- |
|  | Hydroxy-propoxy group | Methoxy group | Acetyl group | Succinyl group | Ratio of acetyl to succinyl |
| HPMCAS-3 | 0.66 | 1.77 | 0.53 | 0.24 | 2.21 |
| HPMCAS-4 | 0.63 | 1.83 | 0.54 | 0.28 | 1.93 |
| HPMCAS-5 | 0.58 | 1.56 | 0.81 | 0.22 | 3.68 |
| HPMCAS-6 | 0.58 | 1.55 | 0.60 | 0.43 | 1.40 |
| HPMCAS-7 | 0.45 | 1.91 | 0.65 | 0.22 | 2.95 |
| HPMCAS-8 | 0.40 | 1.59 | 0.58 | 0.40 | 1.45 |
| HPMCAS-9 | 0.35 | 1.46 | 0.65 | 0.47 | 1.38 |
| HPMCAS-10 | 0.25 | 1.89 | 0.48 | 0.39 | 1.23 |
| HPMCAS-11 | 0.16 | 1.78 | 0.48 | 0.35 | 1.37 |

<Measurement of Glass Transition Temperature of HPMCAS>

The glass transition temperature (Tg) of each of the HPMCAS-1 to 11 was measured using a differential scanning calorimeter ("DSC3200SA", product of Bruker). Described specifically, an inflection-point temperature in an endothermic.exothermic curve was observed when 10 mg of each of the HPMCASs under nitrogen atmosphere was heated to 150° C. from room temperature at a heating rate of 10° C./min, once cooled to 25° C. at a cooling rate of 10° C./min, and then heated again to 230° C. at a heating rate of 10° C./min. In other words, an inflection-point temperature measured at the time of second heating was designated as a glass transition temperature.

Examples 1 to 8 and Comparative Examples 1 to 3

The minimum extrusion temperature of each of the HPMCAS-1 to 11 which had been dried in advance to decrease the water content in the sample to less than 1% by weight, was measured during extrusion from the die outlet port of a vacuum extruder (uniaxial piston melt extruder: "Capilograph" produced by Toyo Seiki Seisaku-sho) under the following conditions: diameter of the die: 1 mm, height of the die: 10 mm, and extrusion rate: 50 mm/min. The results are shown in Table 3.

TABLE 3

|  | HPMCAS | Glass transition temperature (° C.) | Minimum extrusion temperature (° C.) |
| --- | --- | --- | --- |
| Example 1 | HPMCAS-1 | 70 | 110 |
| Example 2 | HPMCAS-2 | 86 | 140 |
| Example 3 | HPMCAS-3 | 104 | 140 |
| Example 4 | HPMCAS-4 | 96 | 140 |
| Example 5 | HPMCAS-5 | 103 | 140 |
| Example 6 | HPMCAS-6 | 101 | 140 |
| Example 7 | HPMCAS-7 | 111 | 150 |
| Example 8 | HPMCAS-8 | 112 | 150 |
| Comp. Ex. 1 | HPMCAS-9 | 123 | 160 |
| Comp. Ex. 2 | HPMCAS-10 | 129 | 180 |
| Comp. Ex. 3 | HPMCAS-11 | 134 | could not be extruded |

The glass transition temperature was low and the minimum extrusion temperature was also low in Examples 1 to 8 for use of HPMCAS having a hydroxypropoxy molar substitution of 0.40 or more, in comparison with Comparative Examples 1 to 3 for use of HPMCAS having a hydroxypropoxy molar substitution of less than 0.4. These results show that because the composition for hot-melt extrusion can be extruded at a lower temperature, an extrusion product can be obtained without deactivation of the drug which will otherwise occur by thermal decomposition.

Examples 9 to 16 and Comparative Examples 4 and 5

Each of the HPMCASs other than HPMCAS-11 which failed to be extruded in Comparative Example 3, and a poorly water-soluble drug, nifedipine (melting point: 172° C.), were mixed at a weight ratio of HPMCAS to nifedipine of 1:0.5 in a mortar to produce a composition for hot-melt extrusion.

The mixture powder was subjected to hot-melt extrusion at 180° C. through a hot-melt extruder (HAAKE™ MiniLab produced by THERMO FISHER SCIENTIFIC™) having the same direction rotation type twin screws (diameter: 5/14 mm, length: 109.5 mm, screw rotation number: 100 rpm, and residence time: 5 minutes). The obtained hot-melt extrusion product was ground with a grinder ("Wonder Blender WB-1" produced by OSAKA CHEMICAL Co., Ltd.) at 2000 rpm, and was sieved through a mesh having mesh size of 30 mesh (opening of 500 μm). The obtained powder was subjected to a dissolution test described in the Japanese Pharmacopoeia 16th Edition.

The dissolution percentage (% by weight) of nifedipine from 270 mg of the powdery composition (containing 90 mg of nifedipine) was measured using 900 mL of the 2nd Liquid (pH 6.8) for disintegration test of the Japanese Pharmacopoeia 16th Edition and a Japanese Pharmacopoeia dissolution tester ("NTR-6100A" produced by TOYAMA SANGO Co., Ltd.) at a paddle rotation of 100 rpm. The amount of nifedipine was determined by obtaining the absorbance of the nifedipine with a UV spectrometer having wavelength of 325 nm and light pathlength of 10 mm, and then by using an absorbance conversion line prepared in advance on basis of absorbance values of known concentrations. The results are shown in Table 4.

TABLE 4

|  | HPMCAS | Nifedipine dissolution percentage (% by weight) *1 | | | | |
| --- | --- | --- | --- | --- | --- | --- |
|  |  | 0 min | 15 min | 60 min | 120 min | 180 min |
| Example 9 | HPMCAS-1 | 0 | 86.3 | 43.6 | 39.2 | 37.5 |
| Example 10 | HPMCAS-2 | 0 | 79.4 | 41.0 | 34.9 | 34.1 |
| Example 11 | HPMCAS-3 | 0 | 78.5 | 95.1 | 96.8 | 90.7 |
| Example 12 | HPMCAS-4 | 0 | 101.2 | 95.9 | 91.6 | 88.5 |
| Example 13 | HPMCAS-5 | 0 | 87.2 | 88.1 | 89.0 | 88.6 |
| Example 14 | HPMCAS-6 | 0 | 93.3 | 48.8 | 37.5 | 35.5 |
| Example 15 | HPMCAS-7 | 0 | 73.3 | 94.2 | 98.5 | 93.3 |
| Example 16 | HPMCAS-8 | 0 | 96.8 | 68.0 | 46.2 | 42.3 |
| Comp. Ex. 4 | HPMCAS-9 | 0 | 99.4 | 53.2 | 41.0 | 38.9 |
| Comp. Ex. 5 | HPMCAS-10 | 0 | 74.4 | 53.8 | 43.2 | 40.1 |

*1: A nifedipine dissolution percentage at each dissolution test time (min) is shown.

A dissolution percentage as high as 73% by weight or more was attained in 15 minutes after starting the test in Examples 9 to 16 for use of HPMASs having a hydroxypropoxy molar substitution of 0.4 or more, as well as in Comparative Examples 4 and 5. A dissolution percentage as high as 88% by weight or more was maintained 60 minutes, 120 minutes, and even 180 minutes after starting the test in Examples 11, 12, 13 and 15 having a molar ratio of acetyl groups to succinyl groups of 1.6 or more. The dissolution percentage was kept high for long period of time presumably because an increase in a molar ratio of acetyl groups to succinyl groups improved the affinity with the poorly water-soluble drug, thereby preventing the poorly water-soluble drug from being recrystallized.

The hot-melt extrusion product was ground using a desk-size grinder ("Wonder Blender WB-1" produced by OSAKA CHEMICAL Co., Ltd.) at 20000 rpm, and was sieved through a mesh having mesh size of 30 mesh (opening of 500 μm). The powder thus obtained was subjected to measurement of an X-ray diffraction pattern. As a result, no crystal peak of nifedipine was observed. It is evident that since the dissolution percentage is markedly high, the composition through hot-melt extrusion forms a solid dispersion having amorphous nifedipine dispersed in the HPMCAS.

Examples 17 to 24 and Comparative Examples 6 and 7

As in Example 9, a composition for hot-melt extrusion was prepared using ascorbic acid as a water-soluble drug. Ascorbic acid has a thermal decomposition temperature of 176° C. and is a model drug which may presumably be deactivated owing to thermal decomposition during hot-melt extrusion.

A composition for hot-melt extrusion was prepared by mixing each of the HPMCASs other than HPMCAS-11 which failed to be extruded in Comparative Example 3, and an ascorbic acid powder at a weight ratio of HPMCAS to ascorbic acid of 1:0.5 in a mortar.

Next, the power mixture obtained above was subjected to hot-melt extrusion at 130° C. or higher with a hot melt extruder (HAAKE™ MiniLab produced by THERMO FISHER SCIENTIFIC™) having the same direction rotation type twin screws (diameter: 5/14 mm, length: 109.5 mm, screw rotation number: 100 rpm, and residence time: 5 minutes). The minimum extrusion temperature of the hot-melt extrusion product thus obtained was measured in the same manner as in Example 1. The obtained hot-melt extrusion product was ground with a grinder ("Wonder Blender WB-1" produced by OSAKA CHEMICAL Co., Ltd.) at 2000 rpm, and was sieved through a mesh having mesh size of 30 mesh (opening of 500 μm). The obtained powder and the composition for hot-melt extrusion before the hot-melt extrusion were subjected to measurements of yellowing index (YI) with SM color computer ("SM-T" produced by Suga Test Instruments Co., Ltd.). The results are shown in Table 5.

TABLE 5

| | | Yellowing index (YI) | | Minimum extrusion temperature (° C.) |
|---|---|---|---|---|
| | HPMCAS used | Before extrusion | After extrusion | |
| Example 17 | HPMCAS-1 | 16.8 | 17.2 | 130 |
| Example 18 | HPMCAS-2 | 16.8 | 18.7 | 145 |
| Example 19 | HPMCAS-3 | 16.8 | 18.9 | 150 |
| Example 20 | HPMCAS-4 | 16.8 | 18.8 | 150 |
| Example 21 | HPMCAS-5 | 16.8 | 18.9 | 150 |
| Example 22 | HPMCAS-6 | 16.8 | 19.0 | 150 |
| Example 23 | HPMCAS-7 | 16.8 | 19.0 | 150 |
| Example 24 | HPMCAS-8 | 16.8 | 19.1 | 150 |
| Comp. Ex. 6 | HPMCAS-9 | 16.8 | 27.8 | 160 |
| Comp. Ex. 7 | HPMCAS-10 | 16.8 | 32.8 | 160 |

In Examples 17 to 24 for use of the HPMCASs having a hydroxypropoxy molar substitution of 0.40 or more, the minimum extrusion temperature was made lower by at least 26° C. than the thermal decomposition temperature (176° C.) of ascorbic acid, and the resulting hot-melt extrusion products remained white appearance and had a yellowing index (YI) of 20 or less, which was substantially the same as the yellowing index of 16.8 for the powder mixture before the extrusion. On the other hand, in Comparative Examples 6 and 7 for use of the HPMCAS as shown in the above table, the minimum extrusion temperature was 160° C., which was higher than that of Examples 17 to 24, and the resulting hot-melt extrusion products changed the appearance from white of starting powder mixtures to brown, and had yellowing index (YI) of largely exceeding over 20, showing that hot-melt extrusion caused the thermal decomposition and deactivation of ascorbic acid.

The invention claimed is:

1. A composition for hot-melt extrusion, comprising a drug and hypromellose acetate succinate having a hydroxypropoxy molar substitution of 0.40 to 1.00.

2. The composition for hot-melt extrusion according to claim 1, wherein the hydroxypropoxy molar substitution is from 0.40 to 0.90.

3. The composition for hot-melt extrusion according to claim 1, wherein the hypromellose acetate succinate has a glass transition temperature (Tg) of 115° C. or lower.

4. The composition for hot-melt extrusion according to claim 1, wherein the hypromellose acetate succinate has a glass transition temperature (Tg) of 70 to 100° C.

5. The composition for hot-melt extrusion according to claim 1, wherein the hypromellose acetate succinate has a methoxy molar substitution from 1.4 to 1.9.

6. The composition for hot-melt extrusion according to claim 1, wherein the hypromellose acetate succinate has an acetyl molar substitution from 0.40 to 0.95.

7. The composition for hot-melt extrusion according to claim 1, wherein the hypromellose acetate succinate has a succinyl molar substitution from 0.10 to 0.60.

8. The composition for hot-melt extrusion according to claim 1, wherein a molar ratio of acetyl groups to succinyl groups in the hypromellose acetate succinate is from 1.6 to 4.0.

9. The composition for hot-melt extrusion according to claim 1, wherein a molar ratio of acetyl groups to succinyl groups in the hypromellose acetate succinate is from 1.8 to 3.8.

10. The composition for hot-melt extrusion according to claim 1, wherein the drug is poorly water-soluble.

11. The composition for hot-melt extrusion according to claim 1, wherein a weight ratio of hypromellose acetate succinate to drug is preferably from 1:0.2 to 1:5.

12. The composition for hot-melt extrusion according to claim 1 further comprising a plasticizer.

13. The composition for hot-melt extrusion according to claim 1 further comprising a surfactant.

14. A method for producing a hot-melt extrusion product, comprising a step of hot-melt extruding a composition for hot-melt extrusion comprising a drug and hypromellose acetate succinate having a hydroxypropoxy molar substitution of 0.40 to 1.0 at a hot-melt temperature of melting temperature of the hypromellose acetate succinate or higher, or at a hot-melt temperature equal to or higher than a temperature at which both the hypromellose acetate succinate and the drug become melted.

15. The method for producing a hot-melt extrusion product according to claim 14, wherein a molar ratio of acetyl groups to succinyl groups in the hypromellose acetate succinate is from 1.6 to 4.0.

16. The method for producing a hot-melt extrusion product according to claim 14, wherein the hot-melting temperature is from 50 to 250° C.

17. The method for producing a hot-melt extrusion product according to claim 14, wherein the hot-melting temperature is from 90 to 190° C.

18. The method for producing a hot-melt extrusion product according to claim 14, wherein the hot-melt extrusion is performed at an extrusion rate of 10 to 100 mm/min.

19. The method for producing a hot-melt extrusion product according to claim 14 further comprising a step of cooling the composition after extrusion.

* * * * *